United States Patent
Connolly et al.

(10) Patent No.: US 11,331,002 B2
(45) Date of Patent: *May 17, 2022

(54) SYSTEM AND METHOD FOR COLLECTING CLINICAL DATA ASSOCIATED WITH A MEDICAL APPARATUS INCLUDING AN IMPLANTABLE DEVICE

(71) Applicant: Vesiflo, Inc., Redmond, WA (US)

(72) Inventors: Kevin M. Connolly, Newton, MA (US); Terence M. Moore, Tomkins Cove, NY (US); Jean-Marc Gery, Los Angeles, CA (US)

(73) Assignee: Vesiflo, Inc., Redmond, VA (US)

( * ) Notice: Subject to any disclaimer, the term of this patent is extended or adjusted under 35 U.S.C. 154(b) by 575 days.

This patent is subject to a terminal disclaimer.

(21) Appl. No.: 16/220,526

(22) Filed: Dec. 14, 2018

(65) Prior Publication Data

US 2019/0117116 A1    Apr. 25, 2019

Related U.S. Application Data

(63) Continuation of application No. 15/837,909, filed on Dec. 11, 2017, now Pat. No. 11,103,154, which is a (Continued)

(51) Int. Cl.
*A61B 5/00* (2006.01)
*A61B 5/07* (2006.01)
(Continued)

(52) U.S. Cl.
CPC .............. *A61B 5/076* (2013.01); *A61B 5/202* (2013.01); *A61B 5/208* (2013.01); *A61B 5/4851* (2013.01);
(Continued)

(58) Field of Classification Search
CPC ......... A61B 5/076; A61B 5/208; A61B 5/202; A61B 5/4851; A61B 5/72; A61B 5/746;
(Continued)

(56) References Cited

U.S. PATENT DOCUMENTS 3,527,220 A * 9/1970 Summers .......... A61M 5/14276
604/153
3,575,158 A    4/1971 Summers
(Continued)

FOREIGN PATENT DOCUMENTS

WO    WO 2005/018708    3/2005

OTHER PUBLICATIONS

International Search Report dated Jul. 29, 2016 for International Application No. PCT/US2016/030409 filed on May 2, 2016 for Vesiflo, 14 pages.

*Primary Examiner* — May A Abouelela
(74) *Attorney, Agent, or Firm* — Cesari and McKenna, LLP

(57) ABSTRACT

A system and method for collecting operation data associated with a medical apparatus including an internal device implanted in a subject and an external device that is magnetically-coupled to and drives the internal device. The medical apparatus may be monitored to obtain raw data associated with the operation of the medical apparatus and one or more calculations may be performed on the raw data, wherein the raw data and/or calculated values may be associated with voiding frequency and voiding volume of the subject. A report may be generated from the raw data and/or calculated values. In addition, one or more signals may be sent to the external device and/or a docking station, or communicated by other means, to indicate to the subject that the operation of the medical apparatus should be altered.

20 Claims, 6 Drawing Sheets

Related U.S. Application Data continuation of application No. 14/747,479, filed on Jun. 23, 2015, now Pat. No. 9,839,373, which is a continuation of application No. 14/712,478, filed on May 14, 2015, now Pat. No. 10,238,314.

(51) Int. Cl.
*A61B 5/20* (2006.01)
*A61F 2/00* (2006.01)
*A61F 2/48* (2006.01)

(52) U.S. Cl.
CPC ............... *A61B 5/72* (2013.01); *A61B 5/746* (2013.01); *A61B 5/7465* (2013.01); *A61F 2/0036* (2013.01); *A61B 5/0022* (2013.01); *A61B 2560/0456* (2013.01); *A61B 2560/0481* (2013.01); *A61F 2/48* (2021.08); *A61F 2/488* (2021.08); *A61F 2210/009* (2013.01); *A61F 2250/0002* (2013.01)

(58) Field of Classification Search
CPC ............... A61B 5/7465; A61B 5/0022; A61B 2560/0456; A61B 2560/0481; A61F 2/0036; A61F 2210/009; A61F 2250/0002; A61F 2002/488; A61F 2002/48; A61F 2/48; A61F 2/488
USPC ........................ 600/573, 576, 583
See application file for complete search history.

(56) References Cited

U.S. PATENT DOCUMENTS

| | | | |
|---|---|---|---|
| 3,810,250 A | 5/1974 | McGregor | |
| 3,810,259 A | 5/1974 | Summers | |
| 3,817,237 A * | 6/1974 | Bolduc | A61F 6/24 128/843 |
| 5,634,878 A * | 6/1997 | Grundei | A61F 2/004 600/30 |
| 5,762,599 A | 6/1998 | Sohn | |
| 6,192,279 B1 * | 2/2001 | Barreras, Sr. | A61N 1/36128 607/117 |
| 6,234,956 B1 * | 5/2001 | He | A61F 2/0018 600/30 |
| 6,417,750 B1 | 7/2002 | Sohn | |
| 7,311,690 B2 * | 12/2007 | Burnett | A61M 5/14276 604/9 |
| 8,398,577 B2 * | 3/2013 | Burnett | A61M 27/002 604/9 |
| 2003/0028082 A1 | 2/2003 | Thompson | |
| 2004/0147871 A1 * | 7/2004 | Burnett | A61M 5/14276 604/9 |
| 2006/0020225 A1 * | 1/2006 | Gerber | A61B 5/202 600/561 |
| 2006/0190051 A1 * | 8/2006 | Gerber | A61N 1/36007 607/41 |
| 2007/0027494 A1 * | 2/2007 | Gerber | A61B 5/686 607/41 |
| 2007/0255176 A1 * | 11/2007 | Rondoni | A61B 5/204 600/573 |
| 2011/0000309 A1 | 1/2011 | Griffiths | |
| 2011/0178455 A1 | 7/2011 | Burnett | |
| 2012/0035496 A1 * | 2/2012 | Denison | A61N 1/36007 600/547 |
| 2012/0109008 A1 * | 5/2012 | Charlez | A61B 5/208 600/573 |

* cited by examiner

SYSTEM AND METHOD FOR COLLECTING CLINICAL DATA ASSOCIATED WITH A MEDICAL APPARATUS INCLUDING AN IMPLANTABLE DEVICE

CROSS-REFERENCE TO RELATED APPLICATIONS

The present application is a continuation of U.S. patent application Ser. No. 15/837,909, which was filed on Dec. 11, 2017, by Kevin M. Connolly et al. for a SYSTEM AND METHOD FOR COLLECTING CLINICAL DATA ASSOCIATED WITH A MEDICAL APPARATUS INCLUDING AN IMPLANTABLE DEVICE, which is itself a continuation of U.S. patent application Ser. No. 14/747,479, which was filed on Jun. 23, 2015, now patented as U.S. Pat. No. 9,839,373 on Dec. 12, 2017, by Kevin M. Connolly et al. for a SYSTEM AND METHOD FOR COLLECTING CLINICAL DATA ASSOCIATED WITH A MEDICAL APPARATUS INCLUDING AN IMPLANTABLE DEVICE, which is itself a continuation of U.S. patent application Ser. No. 14/712,478, which was filed on May 14, 2015, by Kevin M. Connolly et al. for a SYSTEM AND METHOD FOR COLLECTING CLINICAL DATA ASSOCIATED WITH A MEDICAL APPARATUS INCLUDING AN IMPLANTABLE DEVICE, the contents of all of which are hereby incorporated by reference.

BACKGROUND OF THE INVENTION

Field of the Invention

The present invention relates to a medical apparatus, and particularly to a system and method for collecting clinical data associated with a medical apparatus including a device implanted into a subject's body that is magnetically-coupled to an external drive magnet.

Background Information

Routine voiding (i.e., discharging urine) is necessary for good health. However, certain subjects (e.g., patients) with impaired detrusor contractility (IDC) cannot contract the muscles required to push any or all of the urine out of the bladder. Such subjects may utilize a medical apparatus to assist with voiding. Specifically, the medical apparatus may include an internal device (e.g., pump) that is implanted in the subject that controls urine flow and an external device having a drive magnet mounted for rotation external of the subject's body. The driven magnet of the internal device inside the subject is rotated by magnetic-coupling with the drive magnet of the external device. The external driven magnet of the external device may be rotated, for example, by the subject holding down a button (i.e., activator) on the external device, which in turn causes the driven magnet of the internal device to rotate. The subject may hold the button down for a certain period of time that causes the subject to void or discharge urine.

Since many subjects utilize such medical apparatuses while living at their homes and without medical supervision, the subjects may be at an increased risk of bladder-related diseases or conditions. Specifically, if a subject does not void frequently enough or if the subject do not completely empty the bladder by voiding for a long enough period of time, the subject may be at an increased risk of overflow urinary incontinence, urinary tract infections (UTIs), urosepsis and renal reflux. Accordingly, providing information associated with the voiding behavior of a subject (e.g., voiding frequency and voiding volume) to a medical professional may help prevent and/or limit the bladder-related diseases or conditions in the subject.

SUMMARY OF THE INVENTION

Embodiments described herein provide a system and method that collect clinical data associated with a medical apparatus including an internal device implanted in a subject/patient and an external device that is magnetically-coupled to and drives the internal device. Specifically, the magnetically-coupled internal and external devices may be monitored to obtain raw data associated with the operation of the medical apparatus. Such raw data may be associated with a voiding frequency and a voiding volume and include, but is not limited to, the number of times a button of the external device is pressed, and the length of time the button of the external device is held down for during a voiding session.

In addition, one or more calculations may be performed on the raw data. Specifically, the length of time (e.g., seconds) may be multiplied by the device flow rate (e.g., normally 15 cc/second) to determine the voiding volume. Further, an estimated average flow rate value and an estimated real-time flow rate value may be calculated. In addition, the calculated value may be adjusted in order to account for the fact that the subject may hold down the button for a longer period of time than necessary. One or more reports may be generated from the raw data and/or calculated values that may be utilized by a medical professional (e.g., physician or nurse) interested in observing and analyzing the voiding behavior of the subject. In addition, one or more signals may be sent to the external device and/or a docking station (utilized to charge the external device) to alter the manner in which the subject operates the medical apparatus. For example, the signal may cause the docking station to sound an alarm every time the subject is to void, thus ensuring that the voiding frequency of the subject is sufficient. Further, signals may be sent to a mobile phone or other computing device. In addition, the signal may cause a light to illuminate on the external device indicating that the user should hold down the button for a longer period of time, thus ensuring that the desired voiding volume is achieved by the subject.

Advantageously, the voiding behavior of a subject may be monitored by a medical professional without requiring interaction with the subject, where the subject can be informed to alter his voiding behavior based on the analysis of the raw data and/or calculated values. As such, the health of the subject may be maintained or improved.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
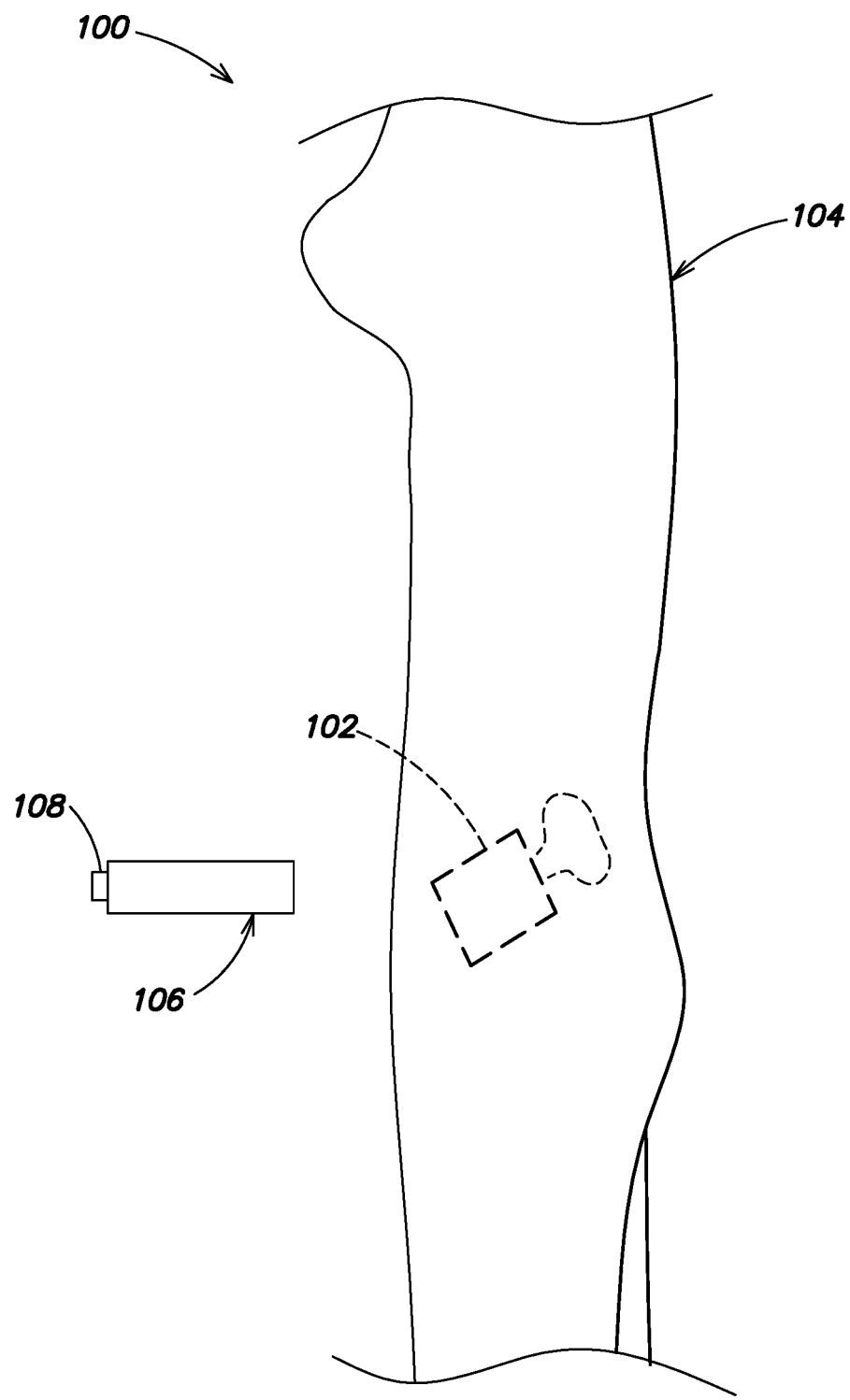
FIG. 1 is an environment of a medical apparatus utilized for one or more embodiments described herein.

FIG. 1 illustrates environment 100 with an valve-pump mechanism arrangement of an external device and an internal device in accordance with one or more embodiment described herein. As illustrated, an internal device 102 (e.g., artificial pump) is implanted in the urethra of a subject 104, for example, a female as depicted in FIG. 1, in order to promote the flow of urine from a non-contractile bladder that requires drainage. It is noted that internal device 102 may be implanted at a particular location and may also be designed and dimensioned based on subject 104 to provide optimum torque. Although reference is made to a female subject, it is expressly contemplated that the device may be utilized with a male subject. Implanted internal device 102 includes a driven magnet mounted for rotation by a drive magnet included within an external device 106 (e.g., the portable unit) that is external to subject 104, wherein the drive magnet and driven magnet may be magnetically-coupled. External device 106 may include a button 108 or other mechanism/activator to cause the drive magnet of external device 106 to rotate. Specifically, to void, subject 104 sits on a toilet (not shown) and holds external device 106 over the lower pelvic area and presses button 108. Pressing of button 108 magnetically activates the driven magnet of internal device 102 that may spin, for example, at 10,000 RPM, and drains the bladder. When button 108 is released, a valve of the internal device (not shown) is engaged, blocking further urine flow. It is noted that the drive magnet and the driven magnet may rotate about the same axis (e.g., the two rotary axes are collinear) as described in U.S. Pat. Nos. 3,575,158 and 3,810,250, or may rotate about different axes as described in U.S. Pat. No. 5,762,599.

Figure 2:
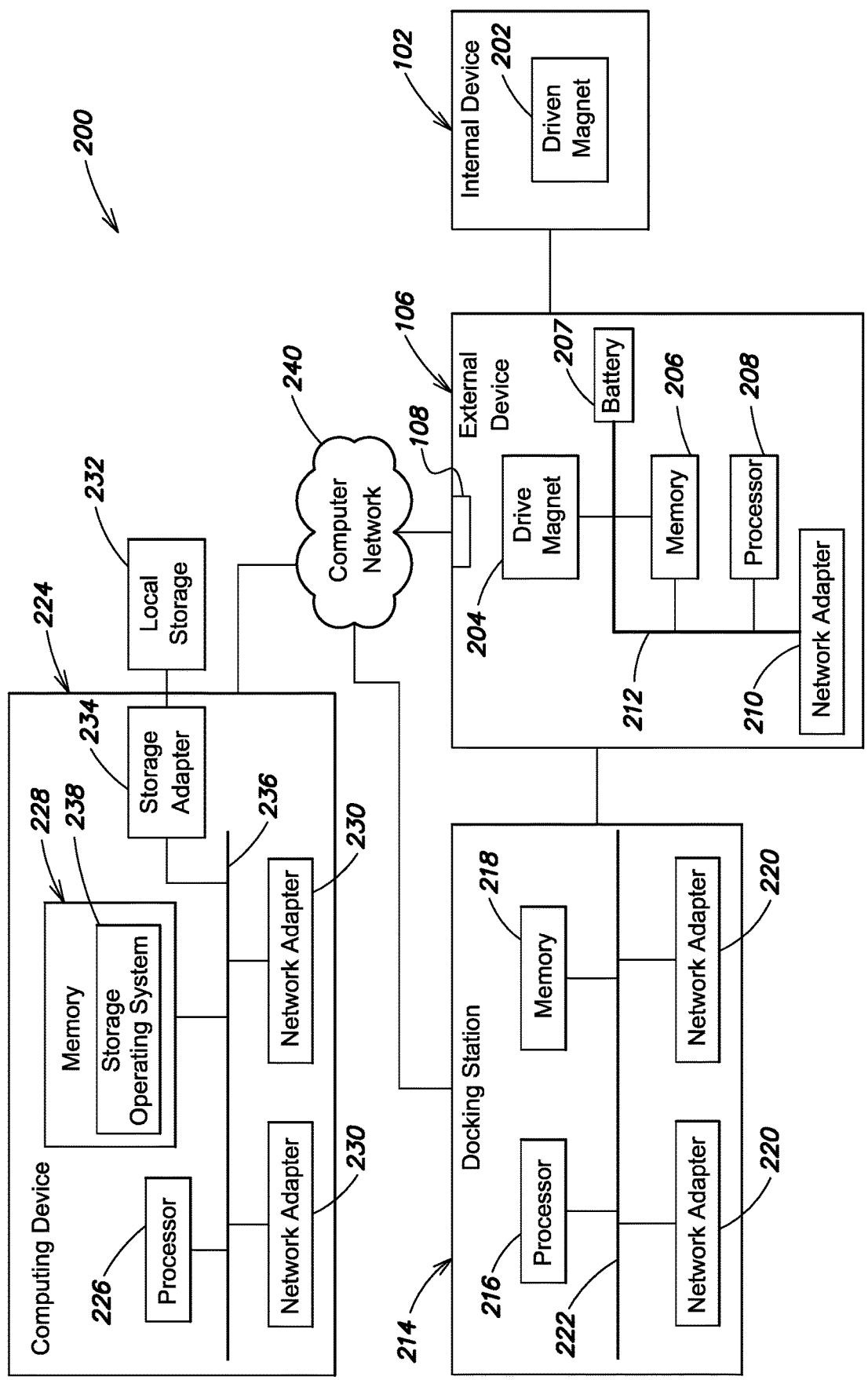
FIG. 2 is a block diagram of the environment for one or more embodiments described herein.

FIG. 2 is a block diagram of an environment 200 for one or more embodiments describe herein. Environment 200 includes internal device 102 that is implanted in the subject's body that includes driven magnet 202. In addition, environment 200 includes external device 106 including drive magnet 204, a memory 206, a battery 207, button 108, a processor 208, and one or more network adapters 210 interconnected by a system interconnect 212, such as a bus. Memory 206 may include storage locations for storing software program code and data associated with one or more embodiments described herein. Processor 208 and adapters 210 may include processing elements and/or logic circuitry configured to execute the software code and manipulate the data stored in memory 206. Specifically, processor 208 may include processing elements and/or logic circuitry to collect raw data associated with the operation of external device 106 and internal device 102.

For example, processor 208 may track of the number of times button 108 is pushed where the number of times is related of voiding frequency. In addition, the processor may track the length of time button 108 is pressed where the length of time is related to voiding volume. For example, a bit may be flipped by processor 208 every time button 108 is pressed and may be flipped back to its original state when button 108 is released.

Alternatively, processor 208 may monitor the current load in external device 106 to determine if external device 106 is coupled to implanted internal device 102 by monitoring the activity of button 108. Specifically, when button 108 is not pressed and external device 106 is not being operated to drive driven magnet 202 of internal device 102, the current load is zero or at a minimal value. However, when button 108 is pressed and external device 106 is being operated to drive driven magnet 202 of internal device 102, the current load in external device 106 increases and reaches a particular level. Thus, the current load information and the length of time the current load is at a particular level may be tracked by processor 208 and used to determine voiding frequency and voiding volume.

In one embodiment, processor 208 may perform one or more calculations on the raw data associated with the operation of internal device 102 and external device 106. Specifically, processor 208 may multiply the length of time (e.g., seconds) by the device flow rate (e.g., normally 15 cc/second) to determine the voiding volume. Further, the processor 208 may utilize the current load to obtain an estimated real-time flow rate value associated with the discharge of urine from the subject 104 utilizing the medical apparatus. Specifically, the higher the load in the external device 106 indicates a higher estimated real-time flow rate while a lower load in the external device indicates a lower estimated real-time flow rate. As such, the processor 208 may utilize a table (not shown), stored in memory 206, that correlates particular load values at the external device with particular estimated real-time flow rate values. Accordingly, processor 208 may index into the table utilizing the determine load value at the external device 106 of the medical apparatus to obtain an estimated real-time flow rate value associated with the discharge of urine from the subject 104 utilizing the medical apparatus. Furthermore, the processor 208 may calculate an estimated average flow rate associated with the discharge of urine from the subject 104 utilizing the medical apparatus. Specifically, the processor may determine the amount of time the subject 104 holds down the button and then divide the volume of urine discharged during a voiding session by the time to calculate the estimated average flow rate value.

In addition, processor 208 may adjust the calculated value in order to account for the fact that subject 104 may press button 108 for a longer period of time than necessary. The raw data and calculated values (i.e., clinical data associated with the medical apparatus) may be stored in memory 206.

Network adapter 210 may include the mechanical, electrical and signaling circuitry needed to connect external device 106 to a docking station 214 (i.e., base station) and a computing device 224 over a computer network 240, which may include a point-to-point connection or a shared medium, such as a local area network. Illustratively, computer network 240 may be embodied as an Ethernet network, a Fibre Channel (FC) network, or a wireless network. External device 106 may communicate with docking station 214 and/or computing device 224 by exchanging discrete frames or packets of data according to pre-defined protocols, such as the Transmission Control Protocol/Internet Protocol (TCP/IP). The packets may be encrypted and formatted in different ways, for example, to ensure safe and reliable transmission over network 240, and to ensure that the transmission of sensitive data complies with rules and regulations set by different governing bodies (e.g., Federal Government and the Health Insurance Portability and Accountability Act). For example, the raw data and/or calculated values may be sent from external device 106 over network 240 to be stored in memory 218 of docking station 214 and/or memory 228 and/or local storage 232 of computing device 224.

Docking station 214 (i.e., base station) includes a processor 216, memory 218, and one or more network adapters 220 interconnected by a system interconnect 222, such as a bus. Docking station 214 may be utilized to power-up or charge battery 207 of external device 106, such that when subject 104 presses down button 108 of external device 106, there is enough power to cause drive magnet 204 of external device 106 to rotate and interact with driven magnet 202 of internal device 102. It is noted that docking station 214 may be plugged into an electrical outlet utilizing a cord (not shown). In addition, external device 106 may be directly coupled to docking station 214 to be charged by the docking station 214, as known by those skilled in the art. Memory 218 may include storage locations that are addressable by processor 216 and adapters for storing software program code and data. For example, memory 218 may store the raw data and/or calculated values.

The processor and adapters may, in turn, include processing elements and/or logic circuitry configured to execute the software code and manipulate the data. In one embodiment, the raw data may be received by docking station 214 from external device 106 over network 240, and processor 216 may perform the calculations on the raw data, as described above. Network adapter 220 may include the mechanical, electrical and signaling circuitry needed to connect docking station 214 to external device 106 and/or computing device 224 over computer network 240. For example, docking station 214 may transmit the raw data and/or calculated values to computing device 224 for storage in memory 228 and/or local storage 232.

Computing device 224 may be a computer, such as a server, that provides storage service relating to the organization of information on local storage 232, such as disks managed by the computing device. Computing device 224 may include a processor 226, memory 228, network adapter 230, local storage 232 and one or more storage adapters 234 connected by a system interconnect 236, such as bus. Local storage 232 may include one or more storage devices, such as disks, solid state disks (SSDs), a database, tape, etc., utilized to store data. For example, local storage 232 may store the raw data and/or calculated values.

Memory 228 may include storage locations that are addressable by the processor and adapters for storing software program code and data. For example, the memory 228 may store the raw data and/or calculated values. Processor 226 and adapters 230 may, in turn, include processing elements and/or logic circuitry configured to execute the software code and manipulate the data structures. For example, processor 226 may receive the raw data from the docking station 214 or the external device 106 over computer network 240 and perform the calculations, as described above.

In addition, processor 226 may generate one or more reports, as described below with reference to FIG. 3, utilizing the raw data and/or calculated values. Reports 300 can be provided to a medical professional (e.g., physician, nurse) who can analyze the raw data and/or calculated values to make one or more decisions and/or determinations. For example, the medical professional may utilize a mobile application executing on a mobile phone, tablet, or other computer device (not shown) to access the raw data, calculated values, and/or generated report, wherein the mobile application is associated with computing device 224. In addition, processor 226 of computing device 224 may generate a notification that is sent to the mobile application to notify the medical profession, for example, that the generated report including the raw data and/or calculated values is available for viewing and analysis.

The medical profession, for example, may utilize the mobile application to analyze the raw data and/or calculated values in the generated report and may then instruct computing device 224 to send one or more signals back to external device 106 and/or docking station 214. For example, the medical professional may determine that based on the analysis of the raw data and/or calculated values in the generated report that subject 104 is not voiding for a long enough period of time or is not voiding frequently enough. Based on such analysis, and utilizing the mobile application, for example, the medical professional may instruct processor 226 to send one or more signals over computer network 240 to docking station 214 and/or external device 106 to advise subject 104 to alter his voiding behavior by voiding more frequently or that a voiding session should occur for a longer period of time. For example, the signal may cause the docking station to sound an alarm every time the subject 104 is to void, thus instructing the subject 104 to void more frequently. In addition, the signal may cause a light to illuminate on the external device 106 indicating that the user should hold down the button 108 during a voiding session for a longer period of time (e.g., for the amount of time the light is illuminated).

Alternatively, the medical professional may utilize the mobile application (e.g., a graphical user interface of the mobile application) to input one or more predefined threshold values. If the raw data and/or calculated values of the generated report meet these one or more predefined threshold values, the one or more signals may be sent to the external device and/or docking station. Specifically, the raw data and/or calculated data may indicate that the subject is voiding for a long enough period of time (e.g., 10 seconds), but that if the subject alters the manner in which he/she voids and operates the medical apparatus and does not continue to void for the same period of time, that the one or more signals should be sent to the external device. For example, the medical professional may specify that if the voiding time by the subject drops below a certain time threshold value (e.g., 8 seconds) or calculated volume is below a volume threshold the one or more signals should be sent to the external device and/or docking station. In addition, or alternatively, the medical professional may specify that if the estimated flow rate is not adequate, that the one or more signals should be sent to the external device and/or docking station. Although reference is made to the utilization of a mobile application, it is expressly contemplated an application resident on memory 228 of the computing device, or an application residing on a different computing device may be utilized.

Storage operating system 238, portions of which are typically resident in memory and executed by the processing elements, functionally invokes storage operations executed by the storage system. It will be apparent to those skilled in the art that other processing and memory means, including various computer readable media, may be used for storing and executing program instructions pertaining to the technique described herein. Also, while the subject matter herein is described in terms of software program code and computers, e.g., applications, programs stored in memory, the code/programs may alternatively be embodied as modules consisting of hardware, software, firmware or combinations thereof. Network adapter 230 may include the mechanical, electrical and signaling circuitry needed to connect computing device 224 to external device 106 and docking station 214 over computer network 240.

Figure 3:
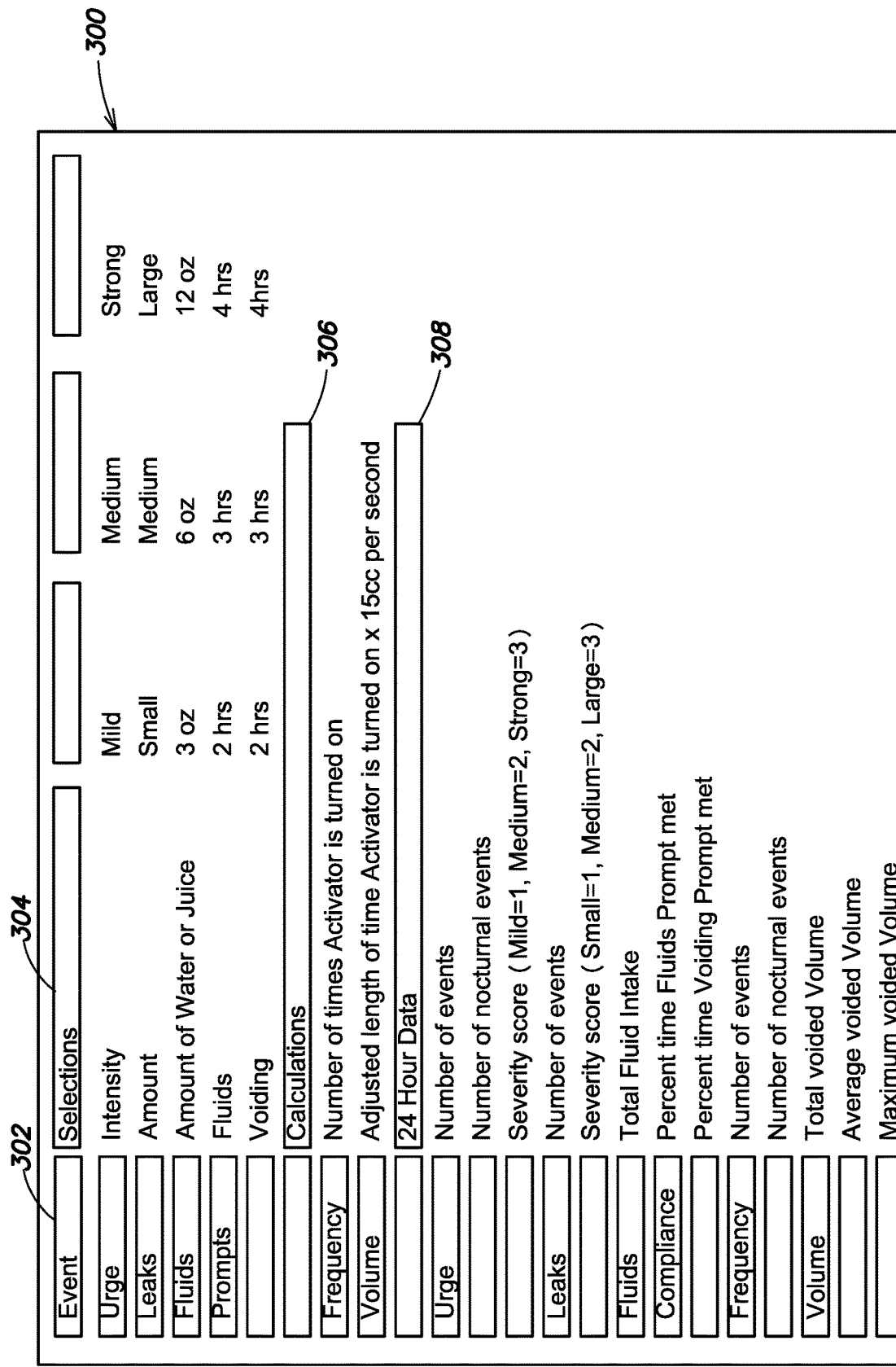
FIG. 3 is a report generated from raw data and/or calculated values for one or more embodiments described herein.

FIG. 3 illustrates an exemplary report 300 that may be generated from the raw data and/or the calculated values for one or more embodiments described herein. In addition, report 300 may be generate based in data provided by subject 204. For example, subject 204 may utilize a mobile application executing on a mobile device of subject 204 to provide relevant information utilized to generate report 300. Such relevant information may include, but is not limited to, an urge subject 204 has to urinate, leaks encountered by subject 204, the liquid intake by subject 204, etc. Report 300 includes a plurality of fields that include, but are not limited to fields for events 302, selections 304, calculations 306, and 24 hour data 308. The events 302 may include, for example and as indicated in report 300, urges, leaks, fluids, and prompts. For example, urge event 302 may have a particular intensity listed in the column for selections 304 that includes "mild", "medium", and "strong." Specifically, a selection may be made to indicate that the subject has a "mild" or "strong" urge/intensity to urinate. More specifically, the selection of a particular intensity for urge event 302 may be selected based on the collected raw data and/or the calculated values. The frequency and volume events 302 may correlate to the calculated values, and the calculated values may be populated in the calculations 306. The leaks events 302 may be associated with the amount or number of leaks the subject encountered in a given time span or period. In addition, other raw data and values may be stored in report 300 as depicted in FIG. 3, such as the frequency and volume voided during a 24 hours period of time. It is expressly contemplated that other data and or calculated values may be stored in generated report 300 and those depicted in report 300 are simply exemplary.

A medical professional may access report 300 utilizing a mobile application or application stored on memory 228 of computing device 224. Report 300 may be utilized by the medical professional to analyze the voiding behavior of the subject. In addition, the medical professional may determine based on report 300, for example, that one or more signals are to be sent to docking station 214 and/or external device 106 to cause subject 104 to alter his voiding behavior as described above. Further, the medical profession may determine based on report 300, for example, that clinical intervention is appropriate. Specifically, one or more signals may be sent to the docking station 214 and/or external device 106 indicating to subject 104 that he/she must see the medical professional.

Figure 4:
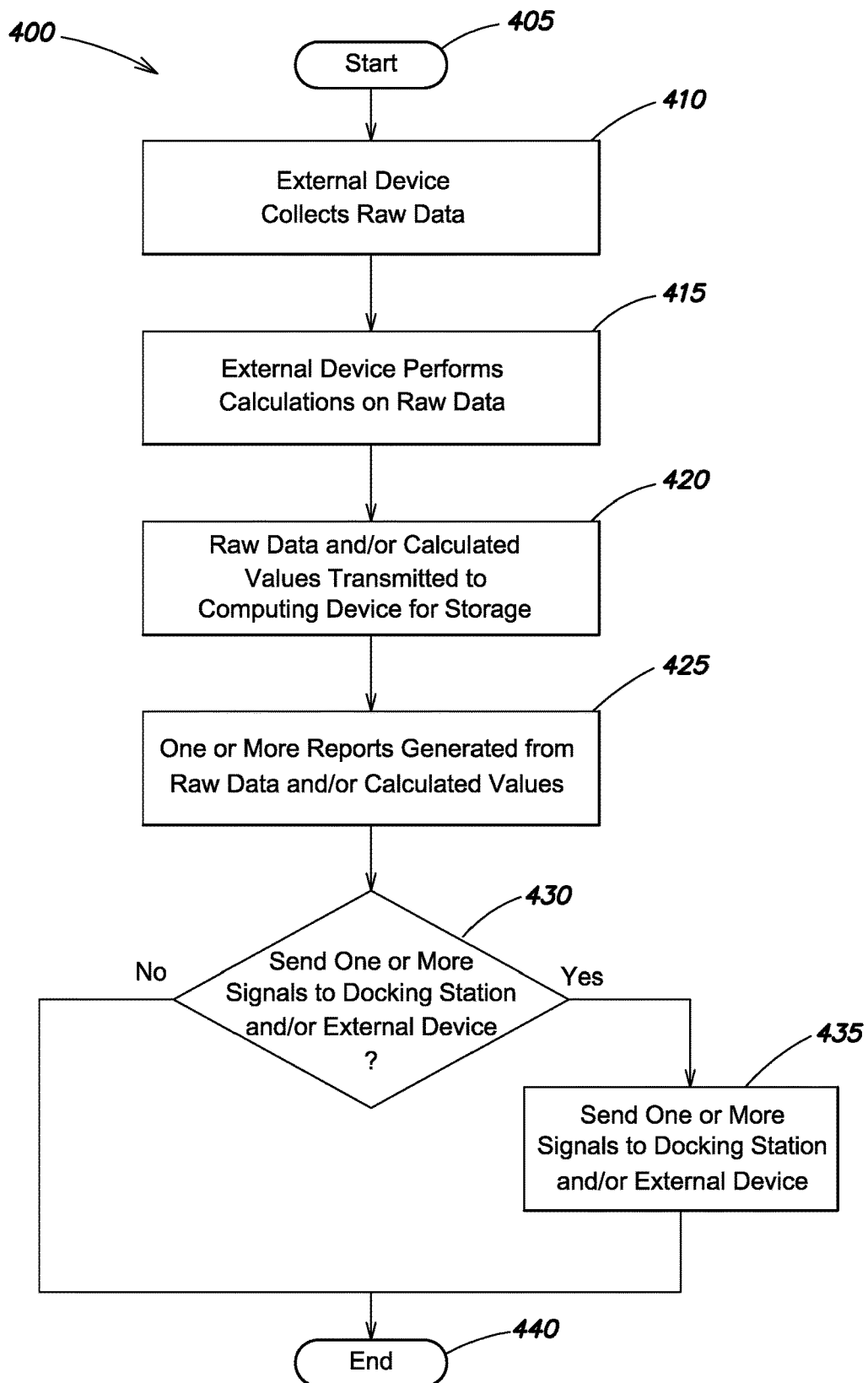
FIG. 4 illustrates a procedure for obtaining clinical data associated with a medical apparatus for one or more embodiments described herein.

FIG. 4 illustrates a procedure for obtaining clinical data associated with a medical apparatus for one or more embodiments described herein. Procedure 400 starts at step 405 and continues to step 410 where the external device collects raw data. During voiding, processor 208 of external device 106 collects raw data associated with the operation of the medical apparatus. For example, processor 208 may track the number of times button 108 is pressed where the number of times is related of the voiding frequency. In addition, processor 208 may keep track of the length of time the button 108 is pressed where the length of time is related of the voiding volume. This raw data may then be stored in memory 206.

The procedure continues to step 415 in which processor 208 of external device 106 performs one or more calculations on the collected raw data. Specifically, processor 208 may multiply the length of time (e.g., seconds) by a nominal flow rate (e.g., 15 cc/second) to determine the voiding volume. Further, the processor 208 may obtain an estimated real-time flow rate values (e.g., utilizing a table) based on the load determined at the external device 106, as described above. Further, the processor 208 may calculate an estimated average flow rate value by dividing the volume of urine discharged during a voiding session by the time the subject 104 holds down button 108, as described above. In addition, processor 208 may adjust the calculated value in order to account for the fact that the subject 104 may hold down the button for a longer period of time than necessary. The procedure continues to step 420, where the raw data and/or the calculated values (i.e., clinical data) are transmitted to computing device 224 for storage. For example, raw data and/or calculated values may be transmitted from external device 106 directly to computing device 224 over computer network 240. Alternatively, raw data and/or calculated values may first be transmitted to docking station 214 for storage (e.g., on memory 218), and then to computing device 224 for storage. The raw data and/or calculated values may be stored on memory 228 of computing device 224 and/or on local storage 232 coupled to computing device 224. In addition, it is noted that the raw data and/or calculated values may be sent to computing device 224 together or independently. For example, after collecting the raw data and before performing the calculations, the raw data may be sent to the computing device 224 for storage, and the calculated values may be sent to the computing device 224 for storage after computation of the calculations.

The procedure continues to step 425 where one or more reports are generated from the raw data and/or calculated values. Specifically, a report 300 is generated by processor 226 of computing device 224 that may include information, such as that depicted in FIG. 3. Generation of a report may cause processor 226 to generate a notification that is transmitted to a mobile application, for example, that is utilized by the medical professional to access and analyze the report.

The procedure continues to step 430 where a determination is made whether one or more signals should be sent to docking station 214 and/or external device 106. Specifically, the raw data, calculated values and/or information in the report may be compared with one or more predefined threshold values. If the raw data, calculated values, or information meet the one or more predefined threshold values, the one or more signals may be sent to docking station 214 and/or external device 106. Alternatively, the medical professional may analyze the raw data, calculated values and/or generated report and determine that the one or more signals should be sent to docking station 214 and/or external device 106, for example, utilizing a mobile application or other application.

If at step 430 it is determined that the one or more signals should be sent to docking station 214 and/or external device 106, the procedure continues to step 435 and the one or more signals are sent from computing device 224 to docking station 214 and/or external device 106 over computer network 240 to alter the manner in which subject 104 operates the medical apparatus. If it is determined that the one or more signals should not be sent to docking station 214 and/or external device 106 (e.g., the voiding behavior of the subject is appropriate), the procedure ends at step 440.

Figure 5:
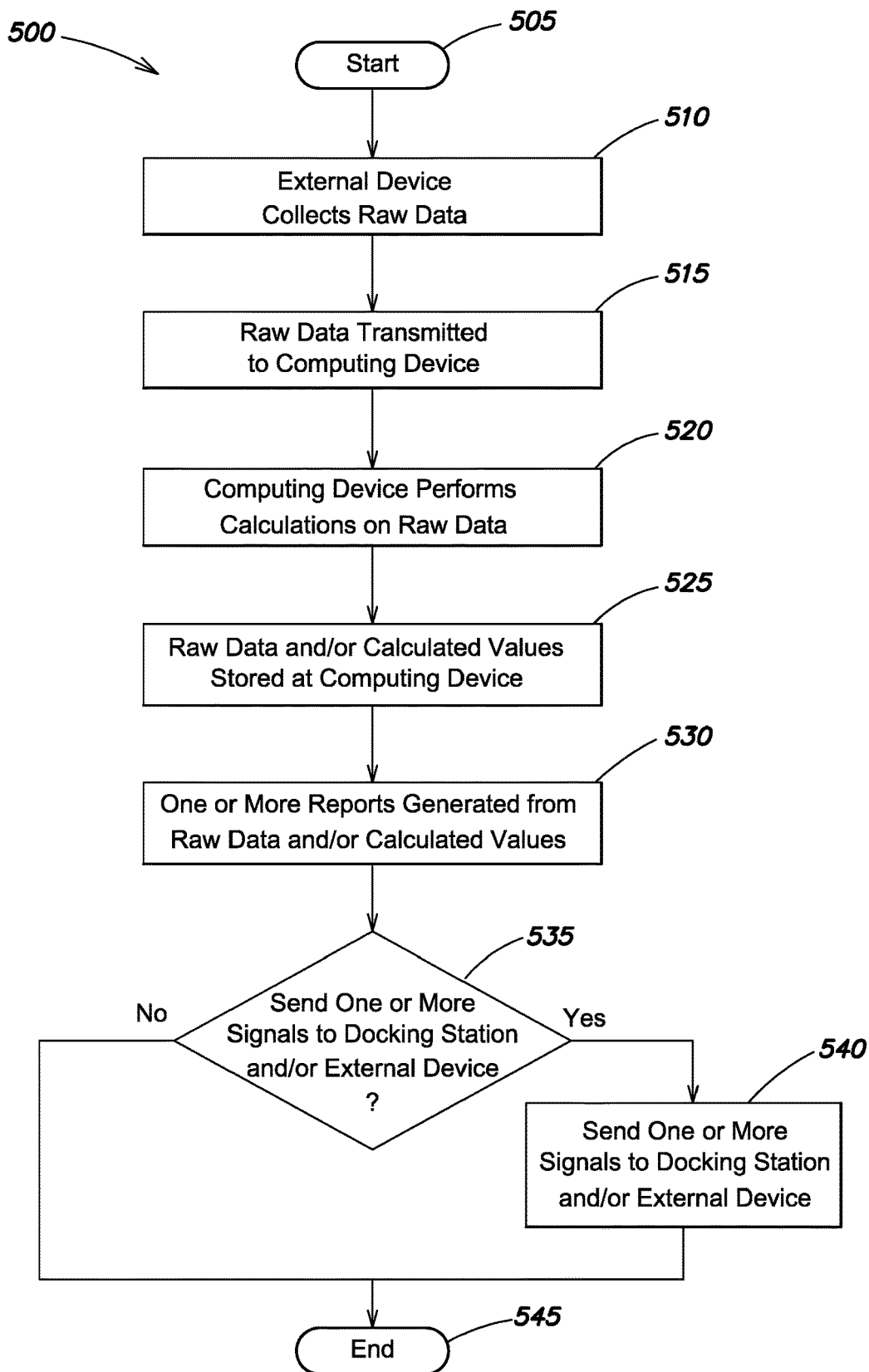
FIG. 5 illustrates a procedure for obtaining clinical data associated with a medical apparatus for one or more embodiments described herein.

FIG. 5 illustrates a procedure for obtaining clinical information for a medical apparatus for one or more embodiments described herein. Procedure 500 starts at step 505 and continues to step 510 where external device 106 collects raw data as described above.

The procedure continues to step 515 and the raw data is transmitted to computing device 224 over computer network 240. Specifically, the raw data may be transmitted from external device 106 directly to computing device 224 over computer network 240. Alternatively, the raw data may be transmitted first to docking station 214 for storage (e.g., on memory 218), and then transmitted to computing device 224. The procedure continues to step 520 where processor 226 of computing device 224 performs one or more calculations on the raw data as described above. The procedure continues to step 525 where the raw data and/or calculated values are stored at computing device 224. For example, the raw data and/or calculated values may be stored on memory 228 and/or local storage 232.

The procedure continues to step 530 where one or more reports are generated from the raw data and/or calculated values. Generation of the report may cause processor 226 to generate a notification that is transmitted to a mobile application, for example, that is utilized by the medical profession to access and analyze the report.

The procedure continues to step 535 where a determination is made whether one or more signals should be sent to docking station 214 and/or external device 106. If at step 535 it is determined that the one or more signals should be sent to docking station 214 and/or external device 106, the procedure continues to step 540 and the one or more signals are sent from computing device 224 to docking station 214 and/or external device 106 over computer network 240 to alter the manner in which subject 104 operates the medical apparatus. If it is determined that the one or more signals should not be sent to docking station 214 and/or external device 106 (e.g., the voiding behavior of the subject is appropriate), the procedure ends at step 545.

Figure 6:
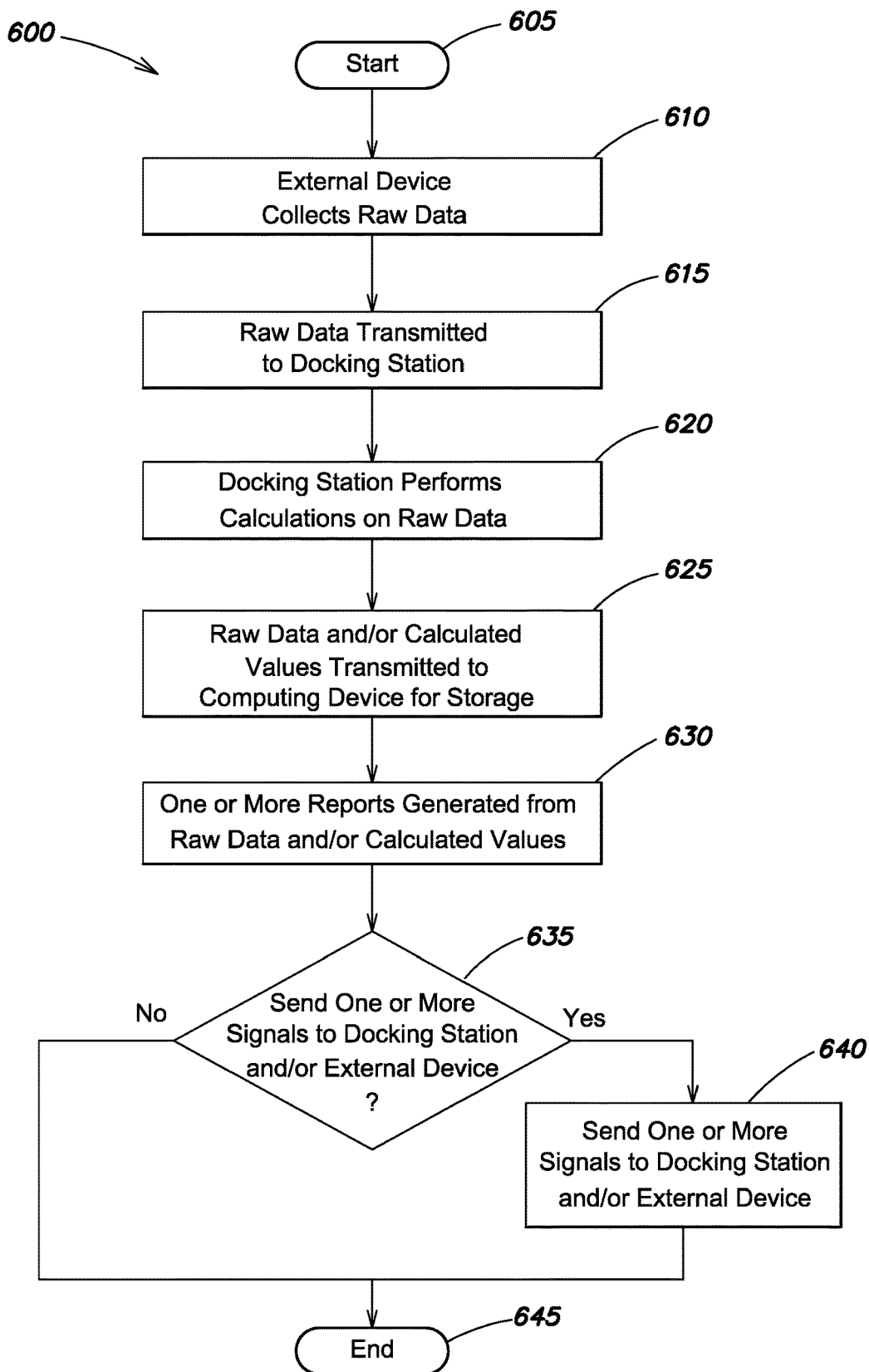
FIG. 6 a procedure for obtaining clinical data associated with a medical apparatus for one or more embodiments described herein.

FIG. 6 illustrates a procedure for obtaining clinical information for a medical apparatus for one or more embodiments described herein. Procedure 600 starts at step 605 and continues to step 610 where external device 106 collects raw data as described above.

The procedure continues to step 615 and the raw data is transmitted to docking station 214 over computer network 240. For example, the raw data may be stored on memory 218 of docking station 214. The procedure continues to step 620 where processor 216 of docking station 214 performs one or more calculations on the raw data as described above. The procedure continues to step 625 where the raw data and/or the calculated values are transmitted from docking station 214 to computer device 224 over computer network 240 for storage. The raw data and/or calculated values may be stored on memory 228 and/or on local storage 232.

The procedure continues to step 630 where one or more reports are generated from the raw data and/or calculated values. Generation of the report may cause processor 226 to generate a notification that is transmitted to a mobile application, for example, that is utilized by the medical profession to access and analyze the report.

The procedure continues to step 635 where a determination is made whether one or more signals should be sent to docking station 214 and/or external device 106. If at step 635 it is determined that the one or more signals should be sent to docking station 214 and/or external device 106, the procedure continues to step 640 and the one or more signals are sent from computing device 224 to docking station 214 and/or external device 106 over computer network 240 to alter the manner in which the subject operates the medical apparatus. If it is determined that the one or more signals should not be sent to docking station 214 and/or external device 106 (e.g., the voiding behavior of the subject is appropriate), the procedure ends at step 645.

The foregoing description described certain example embodiments. It will be apparent, however, that other variations and modifications may be made to the described embodiments, with the attainment of some or all of their advantages. Specifically, it is expressly contemplated that the one or more signals sent to the external device and/or docking station may indicate that the subject to alter the internal device or alter the operation of the medial apparatus in a different manner. For example the subject should hold the external device at a different position external to the subject's body. In addition, a sensor (e.g., a hall sensor) within the external device, for example, may be utilized to detect the magnetic coupling of the internal device and internal device. Data associated with the sensor may then be utilized to obtain the raw data and/or determine the calculated results. Accordingly, the foregoing description is to be taken only by way of example, and not to otherwise limit the scope of the disclosure.

What is claimed is:

1. A medical apparatus comprising:
an internal device configured to be implanted within a subject, the internal device including a driven magnet; and
an external device including a drive magnet, a processor, and a memory, the drive magnet of the external device configured to be magnetically coupled to the driven magnet of the internal device, wherein the memory is coupled to the processor and wherein the processor is configured to:
determine magnetic coupling of the drive magnet and the driven magnet and that the drive magnet of the external device is activated to magnetically rotate the driven magnet of the internal device, and
collect data while the magnetic coupling occurs, wherein the collection of the data is dependent on only the magnetic coupling of the drive magnet with the driven magnet of the medical apparatus.

2. The medical apparatus of claim 1 wherein the processor is further configured to perform one or more calculations utilizing the collected data.

3. The medical apparatus of claim 1 wherein the drive magnet is activated based on a button on the external device being pressed.

4. The medical apparatus of claim 1 wherein the external device is configured to receive one or more signals indicating that a voiding behavior of the subject is to be altered based on a comparison of the data with one or more threshold values.

5. The medical apparatus of claim 4 wherein the data includes one or more of (1) a number of times of the magnetic coupling of the driven magnet and the drive magnet, or (2) a length of time of the magnetic coupling.

6. The medical apparatus of claim 1 wherein the processor is further configured to transmit the data to a computing device over a computer network, wherein the computing device includes a computing processor configured to perform one or more calculations utilizing the data to produce calculated values.

7. The medical apparatus of claim 6 wherein the computing processor is further configured to generate one or more reports based on at least one of the data and the calculated values.

8. The medical apparatus of claim 7 wherein the computing processor is further configured to generate one or more alerts indicating that the one or more reports are available for viewing by a medical professional, wherein the one or more alerts are transmitted to a mobile application executing on a mobile device used by the medical professional.

9. The medical apparatus of claim 1 wherein the processor is further configured to transmit the data to a docking station over a computer network, wherein the docking station includes a docking station processor configured to perform one or more calculations the utilizing the data.

10. A computing device, comprising:
a processor of the computing device; and
a memory of the computing device coupled to the processor, the processor configured to:
receive, over a computer network, data from an external device of a medical apparatus, the external device having a drive magnet magnetically coupled to a driven magnet of an internal device of the medical apparatus,
wherein the internal device is configured to be implanted within a subject,
wherein the data is collected while magnetic coupling of the drive magnet with the driven magnet and the collection of the data is dependent on only the magnetic coupling, and
perform one or more calculations utilizing the data to produce calculated values.

11. The computing device of claim 10 wherein the drive magnet of the external device is activated based on an activation of a button on the external device to rotate the driven magnet of the internal device.

12. The computing device of claim 11 wherein the processor is configured to transmit, over the computer network and to the external device, one or more signals indicating that a voiding behavior of the subject is to be altered based on a comparison of the data with one or more threshold values.

13. The computing device of claim 12 wherein the data includes one or more of (1) a number of times of the magnetic coupling of the driven magnet and the drive magnet, or (2) a length of time of the magnetic coupling.

14. The computing device of claim 10 wherein the processor is further configured to generate one or more reports based on at least one of the data and the calculated values.

15. The computing device of claim 10 wherein the processor is further configured to transmit one or more signals over the computer network to the external device, where the one or more signals indicate that an operation of the medical apparatus is to be altered.

16. The computing device of claim 10 wherein the processor is further configured to transmit one or more signals over the computer network to a docking station of the external device based on a comparison of the data to one or more threshold values, where the one or more signals indicate that an operation of the medical apparatus is to be altered.

17. A method, comprising:
determining, by a processor of an external device of a medical apparatus, that a drive magnet of the external device is activated, wherein the drive magnet is magnetically coupled to a driven magnet of an internal device of the medical apparatus, wherein the internal device is configured to be implanted within a subject;
in response to determining that the drive magnet is activated, collecting, by a processor of the external device, data associated with an operation of the medical apparatus, wherein the collection of the data is dependent on only a magnetic coupling of the drive magnet with the driven magnet; and
storing, within a memory of the external device, the data; and
transmitting, over a computer network, the data from the external device to a computing device.

18. The method of claim 17, wherein the computing device performs one or more calculations utilizing the data to produce one or more calculated values.

19. The method of claim 17 further comprising receiving, at the external device from the computing device, one or more signals indicating that a voiding behavior of the subject is to be altered based on a comparison of the data with one or more threshold values.

20. The method of claim 19 wherein the data includes one or more of (1) a number of times of the magnetic coupling of the driven magnet and the drive magnet, or (2) a length of time of the magnetic coupling.

* * * * *